United States Patent
DiPrete et al.

(10) Patent No.: US 10,549,214 B2
(45) Date of Patent: Feb. 4, 2020

(54) DEVICE FOR RESIDUE HANDLING MINIMIZATION WITH VACUUM-ASSISTED SEPARATIONS

(71) Applicant: Savannah River Nuclear Solutions, LLC, Aiken, SC (US)

(72) Inventors: David P. DiPrete, Evans, GA (US); Donald J. Pak, Martinez, GA (US); Cecilia C. DiPrete, Evans, GA (US); Scott H. Reboul, Aiken, SC (US); Tad S Whiteside, Aiken, SC (US)

(73) Assignee: Savannah River Nuclear Solutions, LLC, Aiken, NC (US)

( * ) Notice: Subject to any disclaimer, the term of this patent is extended or adjusted under 35 U.S.C. 154(b) by 288 days.

(21) Appl. No.: 15/455,262

(22) Filed: Mar. 10, 2017

(65) Prior Publication Data

US 2018/0259492 A1    Sep. 13, 2018

(51) Int. Cl.
| | | |
|---|---|---|
| *B01D 15/22* | (2006.01) | |
| *B01L 3/00* | (2006.01) | |
| *G01N 30/46* | (2006.01) | |
| *G01N 30/06* | (2006.01) | |
| *G01N 1/28* | (2006.01) | |
| *G01N 1/40* | (2006.01) | |

(52) U.S. Cl.
CPC ............... *B01D 15/22* (2013.01); *B01L 3/00* (2013.01); *B01L 3/50255* (2013.01); *G01N 30/06* (2013.01); *B01L 2400/049* (2013.01); *G01N 1/28* (2013.01); *G01N 1/405* (2013.01); *G01N 30/46* (2013.01)

(58) Field of Classification Search
CPC ........ B01D 15/22; G01N 30/26; G01N 30/88; G01N 30/46; G01N 30/06; G01N 1/28; G01N 1/405; G01N 25/14; B01L 99/00; B01L 3/00; B01L 3/50255; B01L 2400/049; Y10T 436/255
See application file for complete search history.

(56) References Cited

U.S. PATENT DOCUMENTS

| | | | |
|---|---|---|---|
| 3,956,125 A | | 5/1976 | Strutt |
| 4,777,021 A | * | 10/1988 | Wertz ................. B01L 3/50255 422/534 |
| 4,787,988 A | | 11/1988 | Bertoncini |
| 4,810,471 A | | 3/1989 | Wachob |
| 4,895,706 A | | 1/1990 | Root |

(Continued)

FOREIGN PATENT DOCUMENTS

| | | |
|---|---|---|
| EP | 1998302 B1 | 11/2012 |
| WO | WO2002096565 | 12/2002 |

OTHER PUBLICATIONS

FIPA GmbH, "Connectors: Vacuum manifolds". Jan. 15, 2019.*

(Continued)

*Primary Examiner* — Benjamin L Lebron
(74) *Attorney, Agent, or Firm* — Dority & Manning, P.A.

(57) ABSTRACT

A device for collection of residue from separation columns. A manifold provides for multiple sample ports that are fluidly connected to a vacuum port by at least one channel. Residue from the separation columns is pulled through the sample ports, into the channel, and then to the vacuum port. From the vacuum port the residue can be moved, under the force of the vacuum, directly to a drain or to a collection vessel connected with a drain.

17 Claims, 10 Drawing Sheets

(56) References Cited

U.S. PATENT DOCUMENTS

| | | | |
|---|---|---|---|
| 5,018,319 A | 5/1991 | Allard | |
| 6,309,608 B1 | 10/2001 | Zhou | |
| 6,656,354 B2 | 12/2003 | Berger | |
| 7,036,537 B2 | 5/2006 | Digianfilippo | |
| 8,409,528 B2 | 4/2013 | Safar | |
| 2004/0258575 A1 | 12/2004 | Perry | |
| 2005/0051471 A1 | 3/2005 | Lane | |
| 2005/0178216 A1* | 8/2005 | Pitt | B01L 3/502 73/863.23 |
| 2005/0252859 A1 | 11/2005 | Hofmann | |
| 2014/0303381 A1 | 10/2014 | Jackson | |

OTHER PUBLICATIONS

Aluminum manifold / multi-channel / for vacuum, FIPA, dated Dec. 28, 2016.
Resprep 12- or 24-Port SPE Manifolds, Restek, dated Dec. 28, 2016.
Microfil Filtration System, Thomas Scientific, dated Dec. 28, 2016.

\* cited by examiner

DEVICE FOR RESIDUE HANDLING MINIMIZATION WITH VACUUM-ASSISTED SEPARATIONS

FEDERAL RESEARCH STATEMENT

This invention was made with Government support under Contract No. DE-AC09-085R22470, awarded by the U.S. Department of Energy. The Government has certain rights in the invention.

FIELD OF THE INVENTION

The subject matter of the present disclosure relates generally to a device for residue collection that is designed to minimize user exposure to the residue.

BACKGROUND OF THE INVENTION

Column separation processes are commonly used in chemical analysis for purposes of e.g., identification of one or more analytes of interest. In general, a vacuum is drawn on a column containing a certain resin. A sample is placed in the column. One or more washes may be applied to the sample in the column. One or more liquid reagents may also be added to the column. The vacuum pulls the liquids through the resin in the column. Different components in the sample are then retained in the resin differently and may separate from each other as they are pulled through the column. These differences allow the analyte of interest to be captured and selectively removed from the resin. The liquids pulled through the column are collected and disposed.

Where the column is used to perform radiochemical separations, the radiological worker is required to perform multiple steps manipulating radioactive materials in difficult environments. For example, conventionally a resin containing column must be connected to a collection reservoir and assembled within a vacuum box. The column is loaded with a radioactive sample and treated with various washes and reagents while a vacuum pulls the reagent through the resin. Once the separation is complete, the vacuum box containing the column is disassembled, the captured liquid in the collection reservoir is disposed, the collection reservoir is replaced, the column is replaced, and the container is reassembled. Each of these steps can increase the risk of exposure and contamination of the worker to the radiological materials.

Accordingly, a device and method of use that minimizes a worker's exposure to one or more dangerous components during separation processes would be useful. Such a device that can be readily manufactured would also be useful. Such a device that had a relatively small and stable footprint would be particularly beneficial.

BRIEF DESCRIPTION OF THE INVENTION

The present invention provides a device for collection of residue from separation columns. A manifold provides for multiple sample ports that are fluidly connected to a vacuum port by at least one channel. Residue from the separation columns is pulled through the sample ports, into the channel, and then to the vacuum port. From the vacuum port the residue can be moved, under the force of the vacuum, directly to a drain or to a collection vessel connected with a drain. Because the manifold does not include internal collection chambers, a worker is not required to place the manifold in a vacuum box, disassemble the manifold, or replace collection chambers in the manifold. As such, the present invention allows a user to minimize exposure to the residue. Additional aspects and advantages of the invention will be set forth in part in the following description, or may be apparent from the description, or may be learned through practice of the invention.

In one exemplary embodiment, the present invention provides a device for vacuum removal of residue. The device includes a manifold defining a longitudinal direction, a top surface, and a bottom surface. A plurality of sample ports are positioned along the top surface of the manifold. A vacuum port is positioned on the manifold. At least one channel fluidly connects the vacuum port with the plurality of sample ports. The sample ports may be arranged in one or more rows extending along the longitudinal direction. For example, the sample ports may be arranged in at least two rows extending along the longitudinal direction. The manifold can define a plurality of side surfaces with the vacuum port positioned on one of the side surfaces. The manifold may be constructed from a plastic block that defines a plurality of sample ports, the vacuum port, and the at least one channel. The plurality of sample ports can be arranged into columns and rows, wherein the rows extend along the longitudinal direction and the columns are orthogonal to the rows. The vacuum port may include a plurality of vacuum ports and each vacuum port of the plurality of vacuum ports may be aligned with one of the columns or rows of sample ports and fluidly connected thereto. Each of the vacuum ports may be fluidly connected with the at least one channel. The at least one channel may include a plurality of legs extending along the longitudinal direction of the manifold. Each leg of the plurality of channels can be positioned directly beneath one of the rows of sample ports. A plurality of separation columns can be provided with each column attached to one of the sample ports. Each separation column may contain e.g., a resin for separating one or more analytes. A collection vessel may be fluidly connected with the vacuum port.

In another exemplary embodiment, the present invention may include a device for vacuum removal of residue. The device includes a manifold constructed of a single block of material and defining a longitudinal direction, a top surface, and a bottom surface. A plurality of sample ports are positioned along the top surface of the manifold and are created by boring into the block of material. A vacuum port is positioned on the manifold and is created by boring into the block of material. At least one channel fluidly connects the vacuum port with the plurality of sample ports and is created by boring into the block of material.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

The use of the same or similar reference numerals in the figures denotes the same or similar features.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 1:
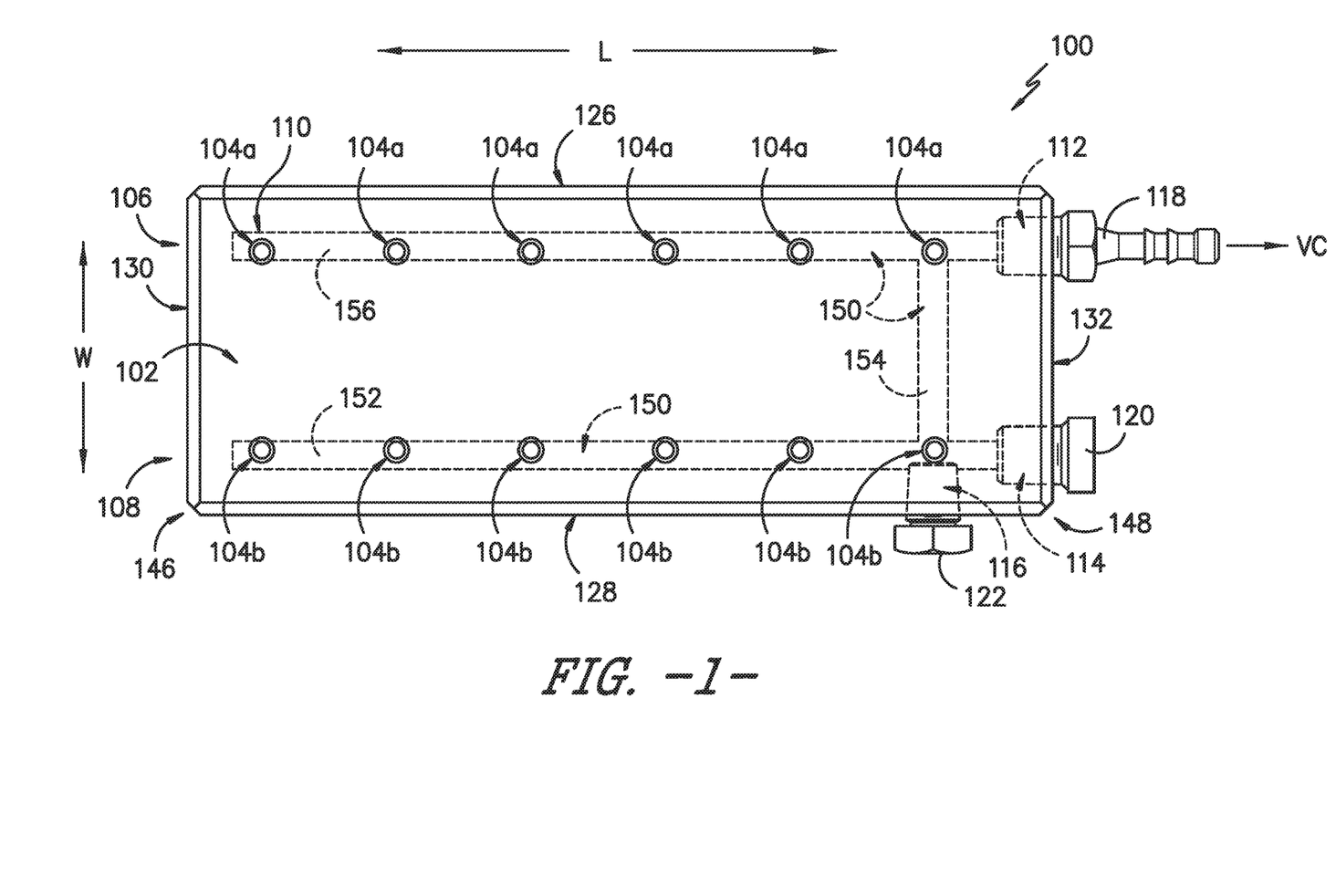
FIG. 1 is a top view of an exemplary embodiment of a device of the present invention.
Figure 2:
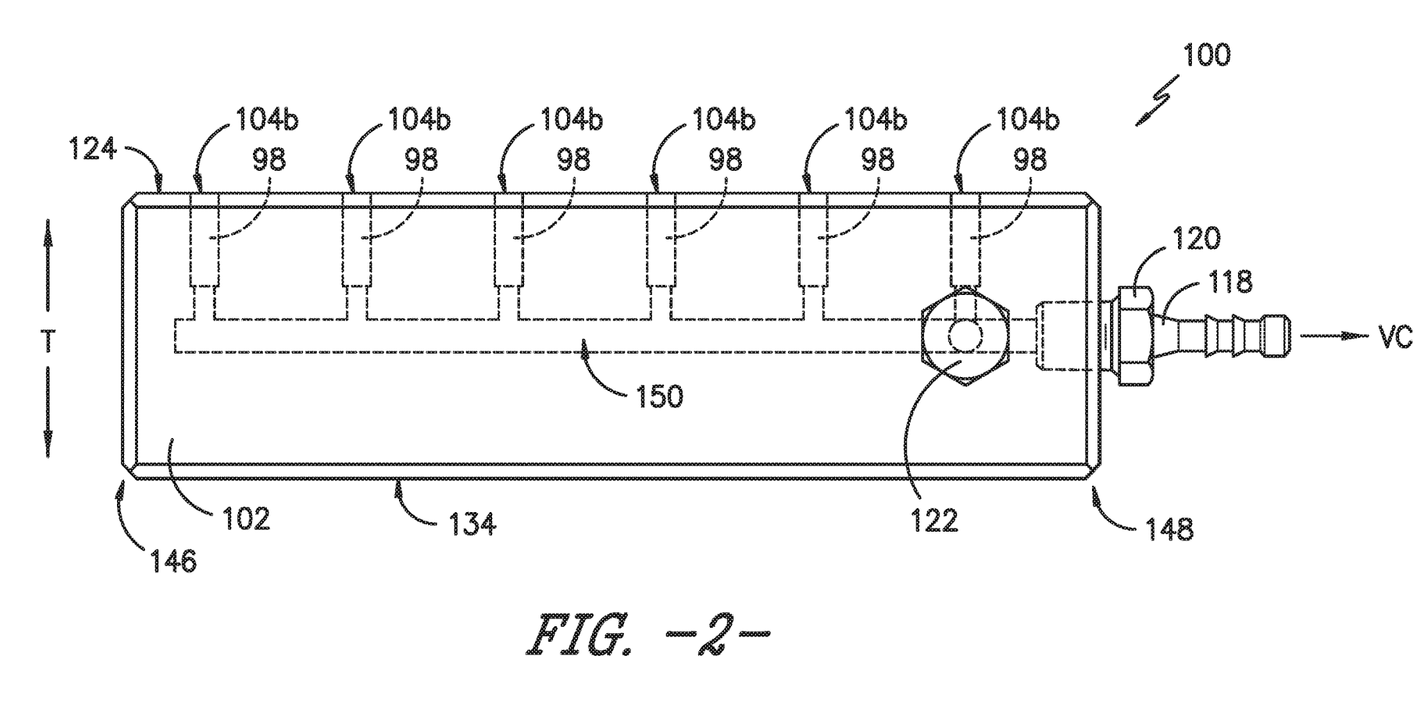
FIG. 2 is side view of the exemplary embodiment of FIG. 1.
Figure 3:
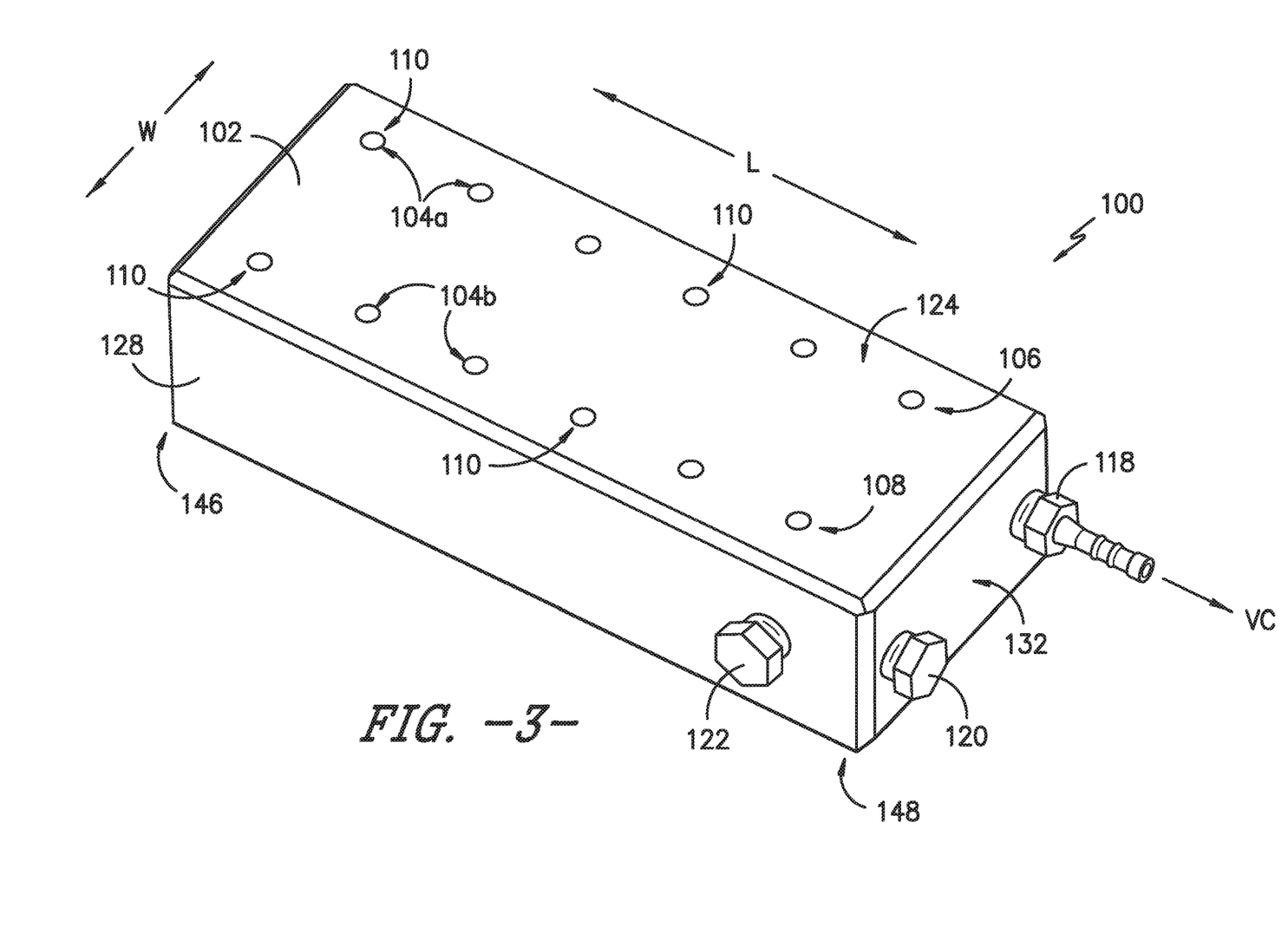
FIG. 3 is a perspective view of the exemplary embodiment of FIGS. 1 and 2.

FIGS. 1, 2, and 3 provide views of an exemplary embodiment of a device 100 for vacuum removal of residue from e.g., a separation column. The present invention may be used with both radioactive and non-radioactive separations where limiting a worker's exposure to one or more hazardous substances is desired. Embodiments of the present invention will be described using separation columns, for example, but it will be understood that the invention could be used with other types of separation devices as well that require removal of e.g., a residue.

Device 100 includes a manifold 102 that, for this embodiment, is constructed from a single block or piece of material. For example, manifold 102 may be formed from a plastic such as polyethylene. Manifold 102 includes a top surface 124 opposite to a bottom surface 134 (FIG. 2). Opposing and parallel sides 126, 128 and 130,132, respectively, make up the periphery of manifold 102 and extend between top and bottom surfaces 124 and 134. Manifold 102 has a length that extends along longitudinal direction L, a width along width direction W, and a thickness along thickness direction T. Manifold 102 extends along longitudinal direction L between first end 146 and second end 148. For this embodiment, top surfaces 124 and 134 are opposing and parallel to each other and are orthogonal to side surfaces 126, 128, 130, and 132. All surfaces 124, 126, 128, 130, 132, and 134 are planar or flat in this embodiment.

Manifold 102 includes a plurality of sample ports 104a, 104b along top surface 124. As shown, in FIGS. 1 and 3, samples ports 104a and 104b are arranged linearly along a first row 106 and a second row 108, respectively, that are parallel to each other and longitudinal direction L. Ports 104a and 104b are also aligned along width direction W into multiple columns 110. Accordingly, as best illustrated in FIG. 1 for this exemplary embodiment, ports 104a and 104b are arranged in multiple rows 104a, 104b, and columns 110 that are orthogonal to each other and would form a grid if connected by lines extending through the ports 104a, 104b.

At least one channel 150 fluidly connects (i.e., provides fluid communication between) each of the sample ports 104a and 104b with each other and with at least one vacuum port 112. As used herein, "fluidly connects" or "fluid communication between" means that a fluid can move between the various ports connected with or along channel 150. Vacuum port 112 is located on side 132 at second end 148 and is aligned with the sample ports 104a along first row 106. For the configuration shown, a vacuum port fitting 118 is installed in vacuum port 112 to provide for connection to a vacuum VC.

Additional vacuum ports 114 and 116 are also included along sides 132 and 128, respectively. Vacuum ports 114 and 116 are also in fluid communication with channel 150. Vacuum port 114 is aligned with sample ports 104b in second row 108. Vacuum port 116 is aligned with a pair of sample ports 104a and 104b in one of the columns 110. For the configuration shown, vacuum ports 114 and 116 are closed with plugs 120 and 122 using complementary threads in ports 114 and 116. Vacuum ports 114 and 116 could be used to apply additional vacuum to channel 150 or to allow for cleaning channel 150.

Channel 150 defines three legs 152, 154, and 156 that are in fluid communication with each other. Legs 152 and 156 extend linearly along longitudinal direction L between ends 146, 148 and are parallel to each other. Leg 154 extends along width direction W and is orthogonal to legs 152 and 156. Leg 152 is positioned directly beneath (along thickness direction T) row 106 of sample ports 104a whereas leg 156 is positioned directly beneath row 108 of sample ports 104b. Leg 156 is positioned near end 148 directly beneath a column 110 of sample ports 104a and 104b.

While channel 150 includes various legs 152, 154, and 156, channel 150 is devoid of chambers, depressions, pits, or other volumes where reside could collect. Instead, for this exemplary embodiment, channel 150 has a uniform and constant diameter among all portions of legs 152, 154, and 156. Furthermore, as shown in FIG. 2, legs 152, 154, and 156 all lie with the same plane or at located at the same level along thickness direction T. In other exemplary embodiments, channel 150 may be provided with a slight incline towards one or more vacuum ports 112, 114, and 116.

In one exemplary aspect of the present invention, sample ports 104a and 104b, vacuum ports 112, 114, and 116, and legs 152, 154, and 156 are all formed or defined by manifold 102. The above-described embodiment of manifold 102 can be created by e.g., drilling or boring side 132 of manifold 102 along longitudinal direction L to simultaneously create vacuum port 112 and leg 156, boring side 132 along longitudinal direction L to simultaneously create vacuum port 114 and leg 152, and boring side 128 along width direction W to simultaneously create vacuum port 116 and leg 154. Each leg 152, 154, and 156 may then be tapped to create ports 112, 114, and 116 and provided with e.g., complementary threads for receipt of fitting 118, plug 120, and plug 122, respectively. Top surface 124 can be bored along thickness direction T to create sample ports 104a and 104b connected with legs 152 and 156 by connecting shafts 98 (FIG. 2) that are parallel to each other and thickness direction T and are orthogonal to the legs of channel 150. Thus, as will be understood by one or ordinary skill in the art using the teachings disclosed herein, manifold 102 can be readily constructed by boring and threading e.g., a single piece of plastic material. In other embodiments, manifold 102 may be created by molding the required features as well.

Figure 4:
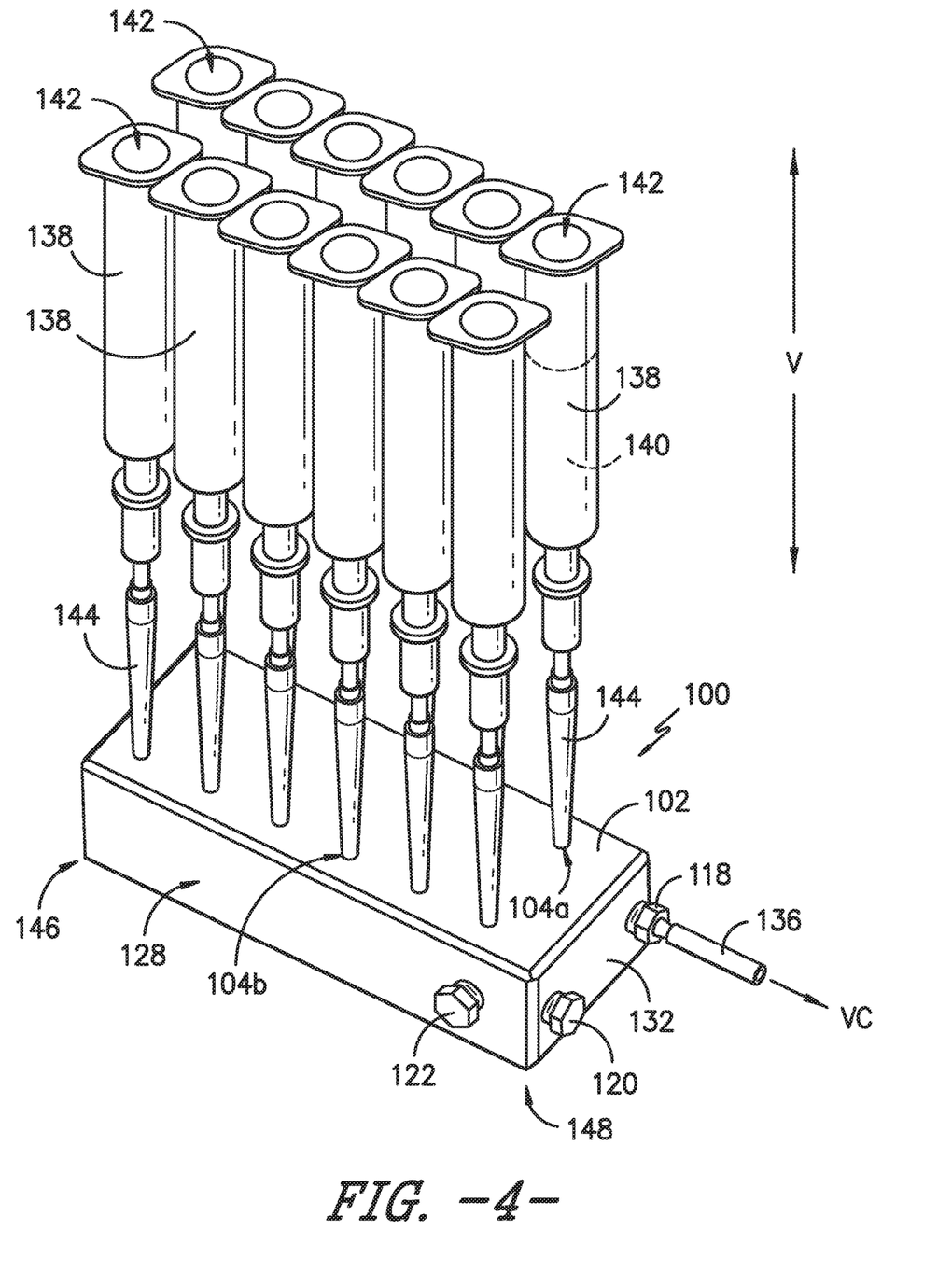
FIG. 4 is a perspective view of the exemplary embodiment of FIGS. 1 through 3 with multiple, exemplary separation columns attached.

Referring now to FIG. 4, an exemplary use of device 100 is depicted. More particularly, a plurality of separation columns 138 are connected with manifold 102. More particularly, each separation column 138 is attached to connector 144 inserted into one of sample ports 104*a* or 104*b*. The overall size of manifold 102 (particularly its width and length) can be selected to minimize the footprint of manifold 102 while also providing the stability needed. For this exemplary embodiment, columns 138 are provided as a syringe-like barrel or cylinder. A resin 140 is located in each separation column 138. Different resins 140 may be used in different separation columns 138. A vacuum line or tube 136 is attached to vacuum port fitting 118 to provide a vacuum VC, which in turn is fluidly communicated by channel 150 to each sample port 104*a*, 104*b* and then to resin 140 in each separation column 138.

Samples may be introduced into each separation column 138 by column opening 142 along with one or more washes or reagents in various steps as desired. Residue in the form of e.g., liquid provided by the washes and/or reagents that also may include various components from the sample are pulled through resin 140 and connector 144 downwardly along vertical direction V into channel 150 by vacuum VC. Notably, manifold 102 lacks a collection chamber or other cavity for the capture and collection of the residue.

Instead, vacuum VC pulls residue through one or more legs 152, 154, and 156 of channel 150, through vacuum port fitting 118 and into vacuum line 136 for direct removal to e.g., a drain or a collection funnel where the residue can be readily disposed without further handling by a worker. Because manifold 102 lacks a capture or collection volume, further use of manifold 102 does not require additional handling of the residue because such is already removed from manifold 102 by vacuum VC. In addition, manifold 102 does not require installation and removal from e.g., a vacuum body. Separation columns 138 can be readily removed for collection of an analyte of interest from residue 140.

Figure 5:
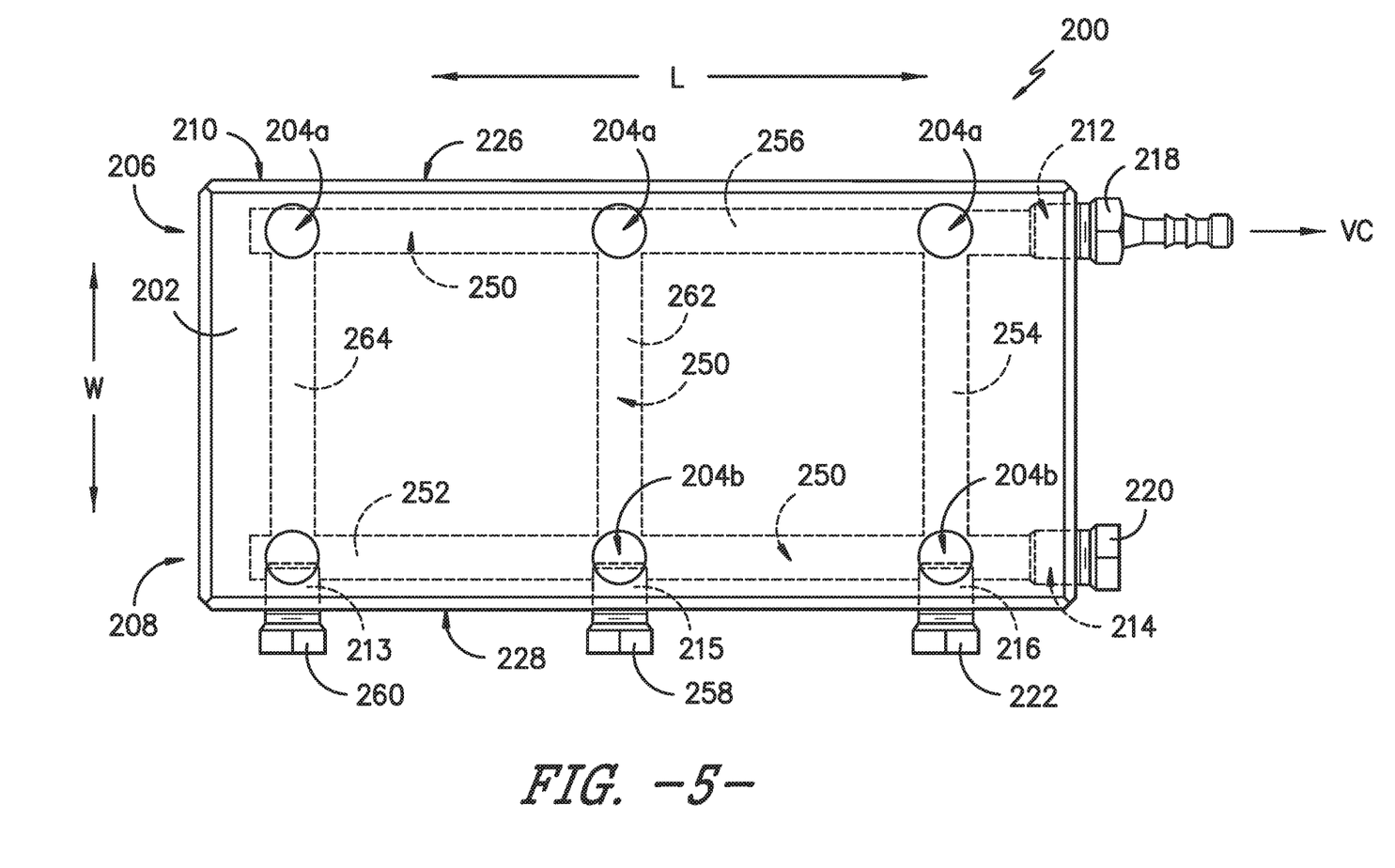
FIG. 5 is a top view of another exemplary embodiment of a device of the present invention.
Figure 6:
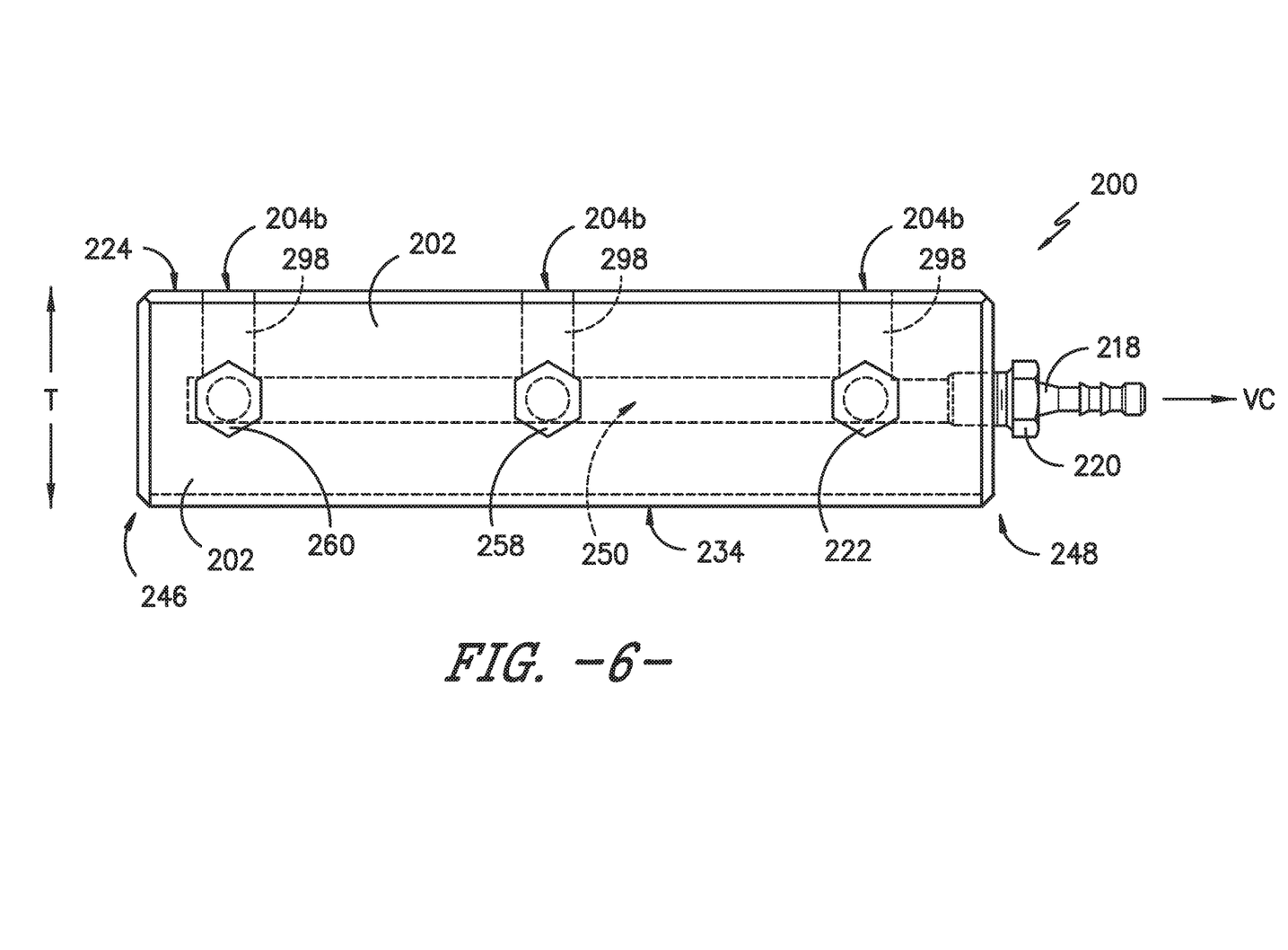
FIG. 6 is side view of the exemplary embodiment of FIG. 5.
Figure 7:
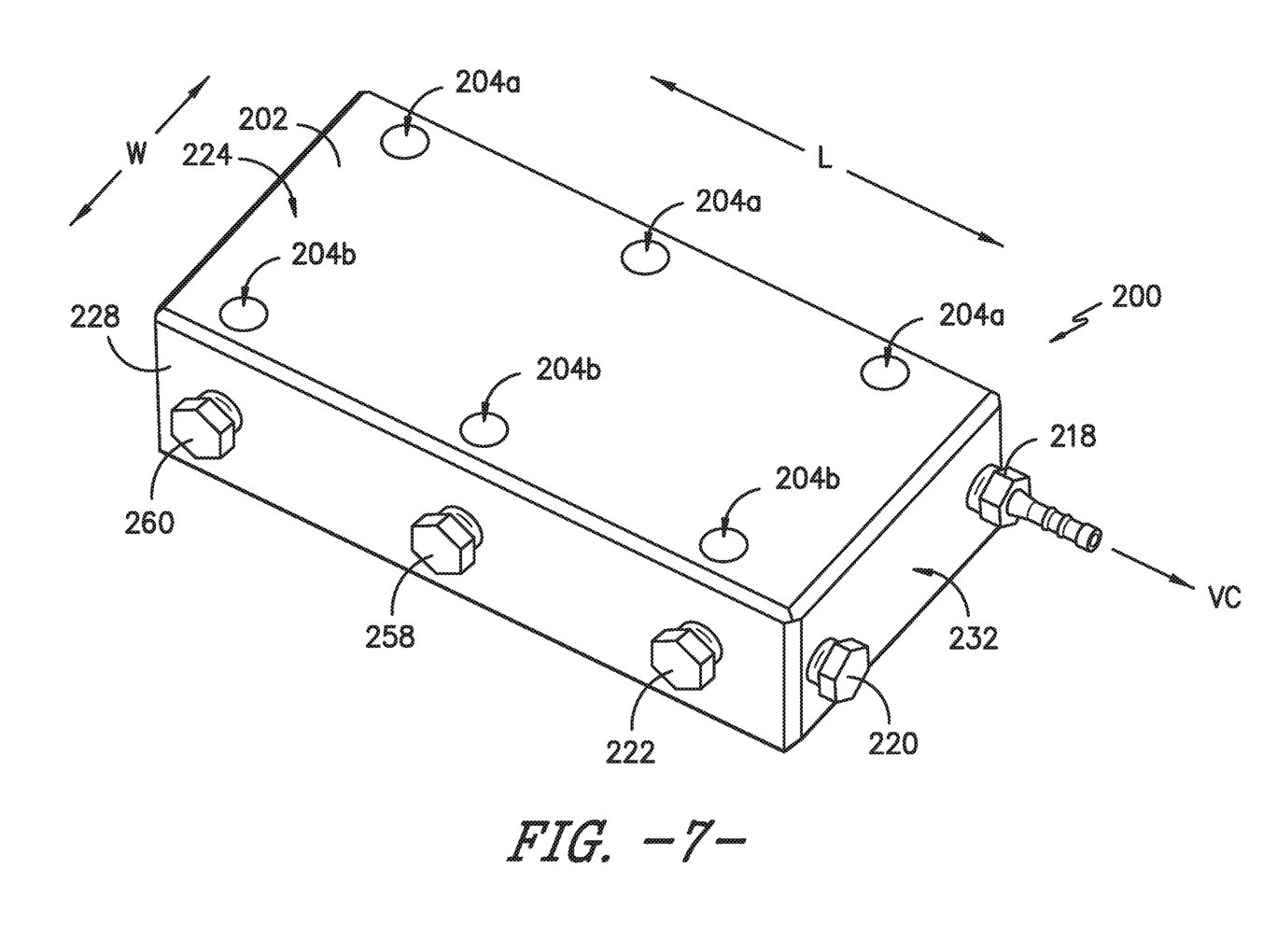
FIG. 7 is a perspective view of the exemplary embodiment of FIGS. 5 and 6.

FIGS. 5, 6, and 7 illustrate another exemplary embodiment the invention with a device 200 for vacuum removal of residue similar to the device 100 of FIGS. 1, 2, and 3. However, the manifold 202 of device 200 in FIGS. 5, 6, and 7 includes only 6 sample ports 204*a* and 204*b* whereas manifold 102 includes 12 sample ports 104*a* and 104*b*. As will be understood by one of skill in the art using the teachings disclosed herein, the number of ports can be selected as desired based on e.g., the intended usage of the device. In addition, manifold 202 includes a channel 250 constructed from legs 252, 254, 256, 262, and 264. Legs 252 and 256 are parallel to each other along longitudinal direction L whereas legs 254, 262, and 264 are parallel to each other along width direction W. Legs 252 and 256 are orthogonal to legs 254, 262, and 264. Manifold 202 may be constructed by e.g., boring or drilling to create the legs 252, 254, 256, 262, and 264 and ports 212, 213, 214, 215, and 216 as previously described.

Figure 8:
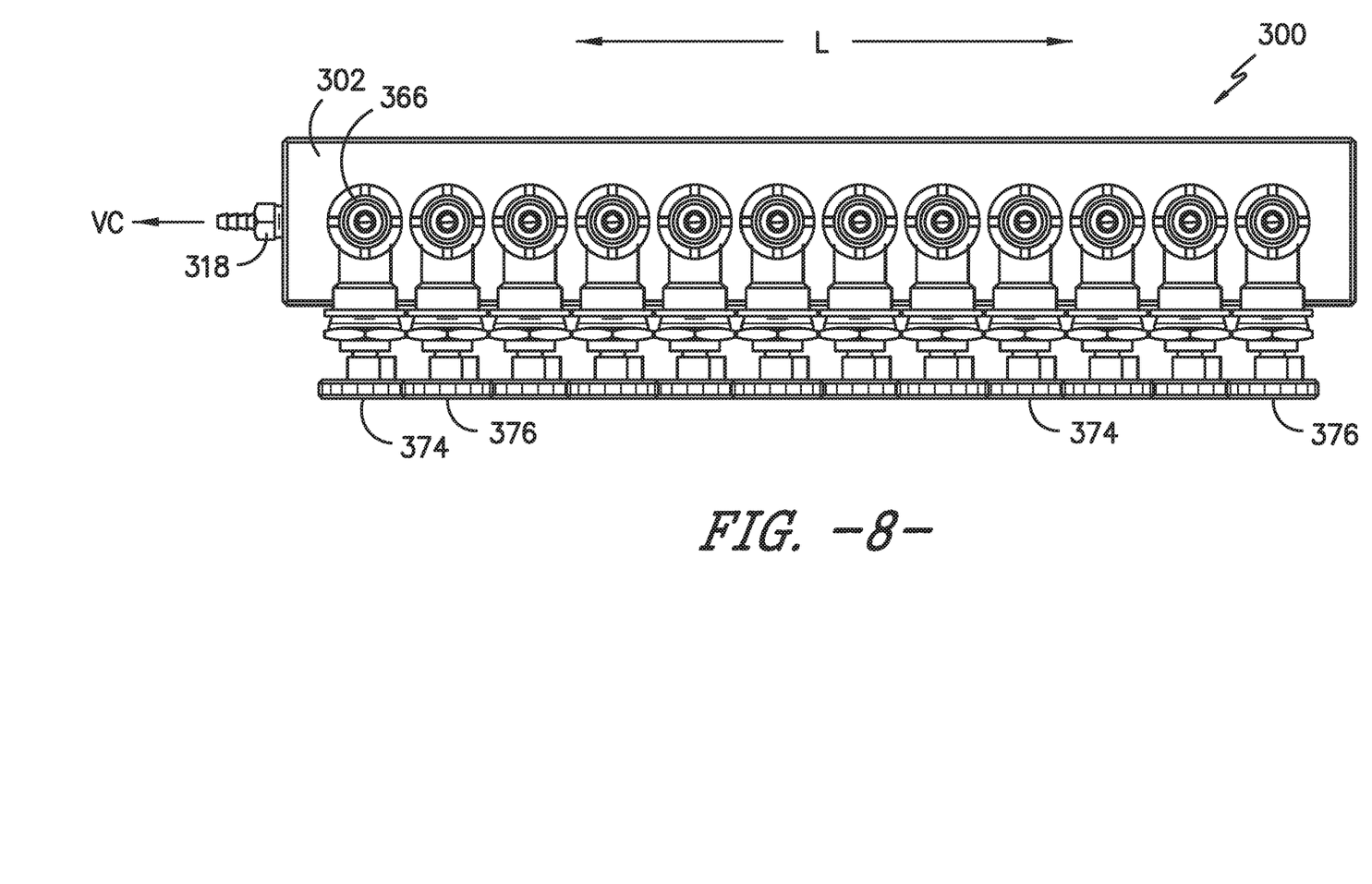
FIG. 8 is a top view of another exemplary embodiment of the present invention.
Figure 9:
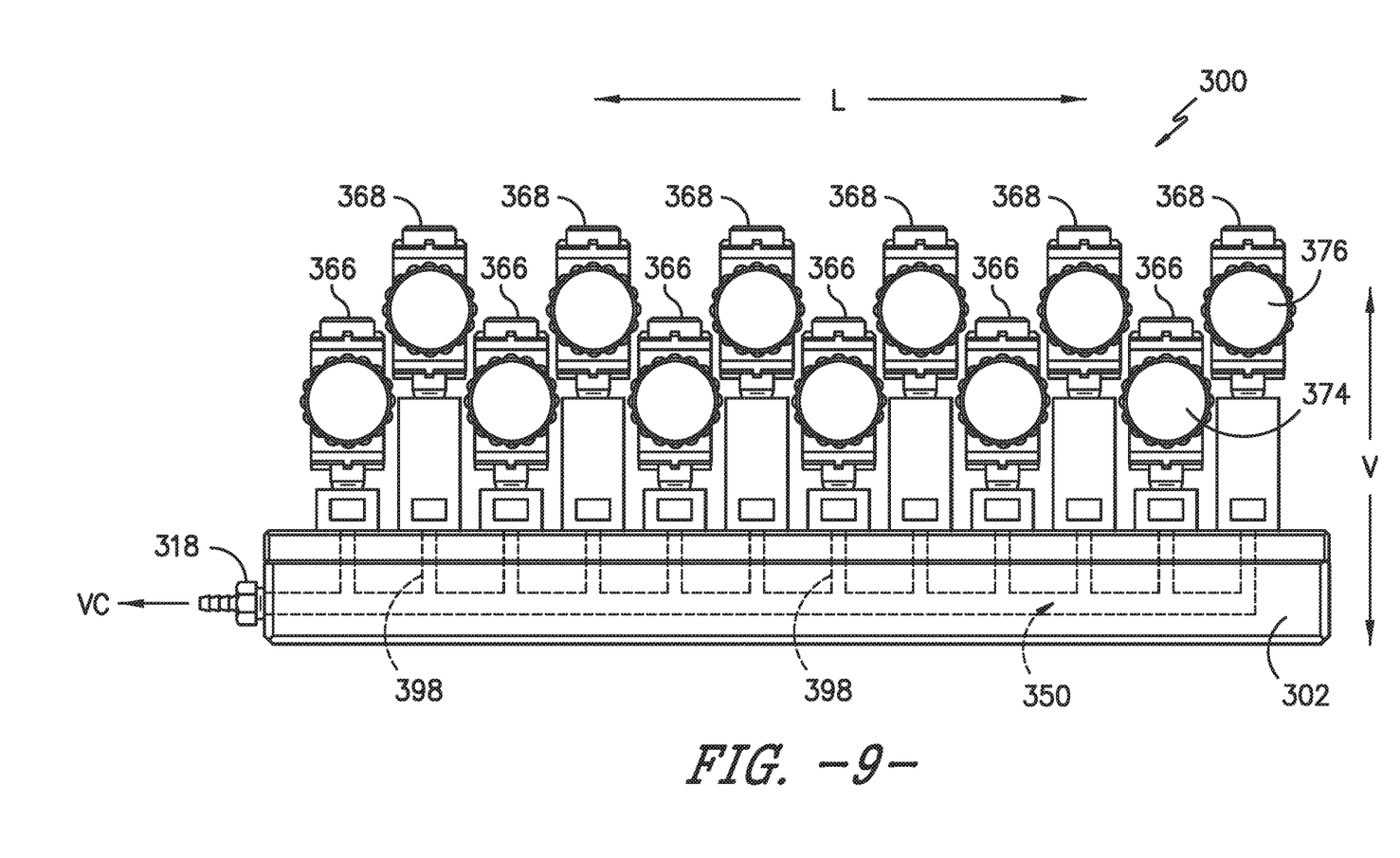
FIG. 9 is side view of the exemplary embodiment of FIG. 8.
Figure 10:
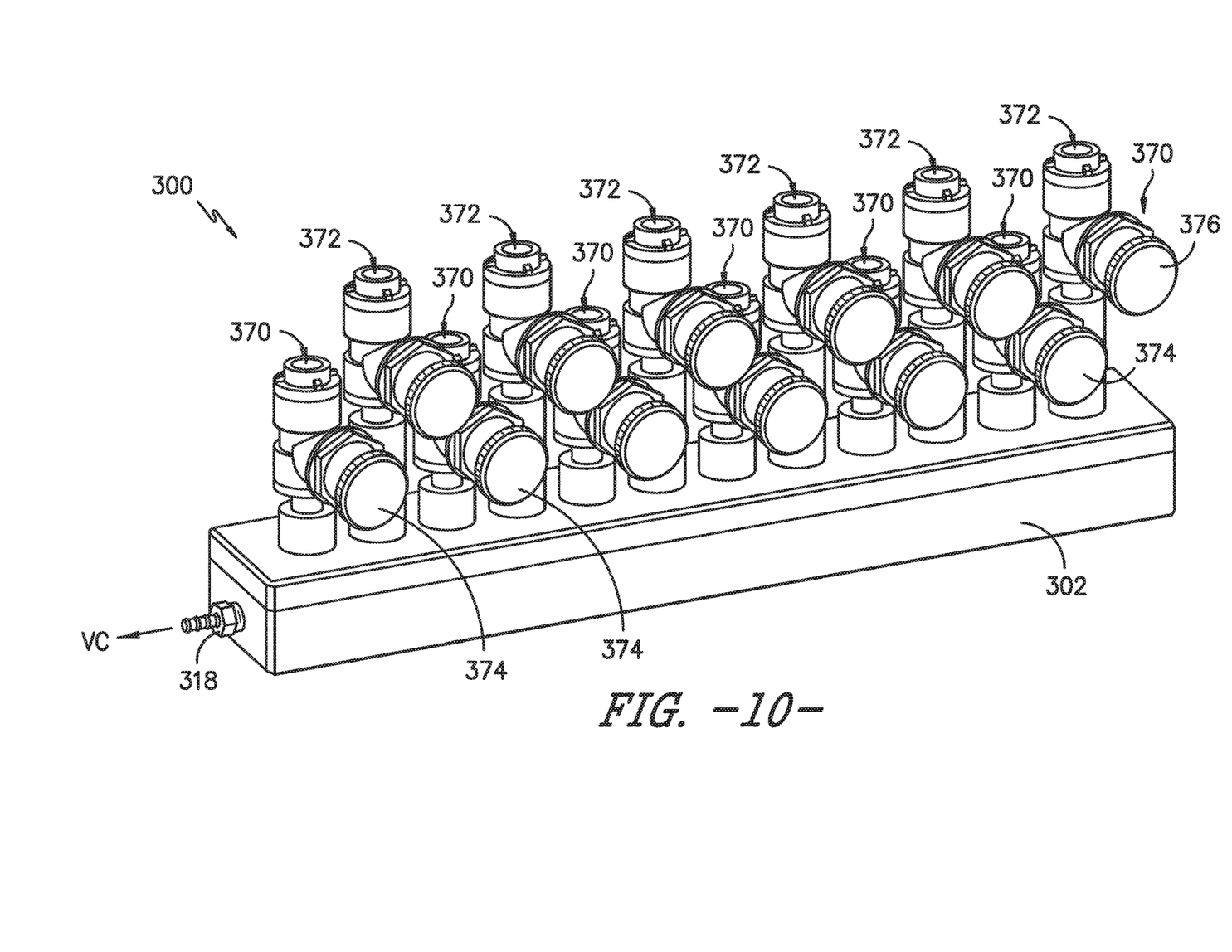
FIG. 10 is a perspective view of the exemplary embodiment of FIGS. 8 and 9.

FIGS. 8, 9, and 10 illustrate another exemplary embodiment of a device 300 for vacuum removal of residue from e.g., separation columns or other separation devices. Manifold 302 includes a channel 350 that extends along longitudinal direction L and is connected by shafts 398 to a plurality of ports that are each fitted with valves 366 and 368. Valves 366 and 368 are adjacent to one another and alternate in height along vertical direction V with valves 368 being slightly higher than valves 366. Such alternating arrangement allows for a more dense arrangement thereby decreasing the footprint of manifold 302. Each valve 366, 368 includes a port 370, 372, respectively, for connecting to e.g., a separation column. Dials or knobs 374, 376 allow for the individual adjustment of valves 366, 368 to selectively control the amount of vacuum VC applied to each port 370, 372. As with previous embodiments, channel 350 lacks any chambers or recesses where residue may collect and, instead, is a constant diameter along longitudinal direction L. As shown in FIG. 9, channel 350 is linear along longitudinal direction L and lies in a plane parallel to longitudinal direction L. As slight incline to assist with draining residue towards vacuum port fitting 318 may be used.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A device for vacuum removal of residue, comprising:
 a manifold defining a longitudinal direction, a top surface, and a bottom surface, the manifold defining a thickness direction extending between the top surface and the bottom surface;
 a plurality of sample ports positioned along the top surface of the manifold;
 a vacuum port positioned on the manifold; and
 at least one channel fluidly connecting the vacuum port with the plurality of sample ports, the at least one channel comprising a plurality of legs extending along the longitudinal direction and fluidly connected to each other, the plurality of legs having a uniform and constant diameter and located at a same level along the thickness direction.

2. The device for vacuum removal of residue as in claim 1, wherein the plurality of sample ports are arranged in one or more rows extending along the longitudinal direction.

3. The device for vacuum removal of residue as in claim 1, wherein the plurality of sample ports are arranged in at least two rows extending along the longitudinal direction.

4. The device for vacuum removal of residue as in claim 1, wherein the manifold defines a plurality of side surfaces, and wherein the vacuum port is positioned on one of the side surfaces.

5. The device for vacuum removal of residue as in claim 1, further comprising a plastic block that defines the manifold, the plurality of sample ports, the vacuum port, and the at least one channel.

6. The device for vacuum removal of residue as in claim 1, wherein the plurality of sample ports are arranged into columns and rows, wherein the rows extend along the longitudinal direction and the columns are orthogonal to the rows.

7. The device for vacuum removal of residue as in claim 6, wherein the vacuum port comprises a plurality of vacuum ports, each vacuum port of the plurality of vacuum ports aligned with one of the columns or rows of the plurality of sample ports and fluidly connected thereto.

8. The device for vacuum removal of residue as in claim 7, wherein the plurality of vacuum ports are fluidly connected with the at least one channel.

9. The device for vacuum removal of residue as in claim 7, wherein the plurality of legs are devoid of depressions or pits where residue could collect.

10. The device for vacuum removal of residue as in claim 9, wherein each leg of the plurality of legs is positioned directly beneath one of the rows of the plurality of sample ports.

11. The device for vacuum removal of residue as in claim 9, further comprising a plurality of separation columns, each of the plurality of separation columns attached to one of the plurality of sample ports, each separation column containing a resin for separating one or more analytes.

12. The device for vacuum removal of residue as in claim 9, further comprising a collection vessel fluidly connected with the vacuum port.

13. A device for vacuum removal of residue, comprising:
a manifold constructed of a single block of material and defining a longitudinal direction, a top surface, and a bottom surface;
a plurality of sample ports positioned along the top surface of the manifold and created by boring into the block of material;
a vacuum port positioned on the manifold and created by boring into the block of material; and
at least one channel fluidly connecting the vacuum port with the plurality of sample ports and created by boring into the block of material, the at least one channel comprising a plurality of legs extending along the longitudinal direction and fluidly connected to each other, the plurality of legs having a uniform and constant diameter and located at a same level along the thickness direction.

14. The device for vacuum removal of residue as in claim 13, wherein the plurality of sample ports are arranged in one or more rows extending along the longitudinal direction.

15. The device for vacuum removal of residue as in claim 13, wherein the plurality of sample ports are arranged in at least two rows extending along the longitudinal direction.

16. The device for vacuum removal of residue as in claim 13, wherein the manifold defines a plurality of side surfaces, and wherein the vacuum port is positioned on one of the side surfaces.

17. The device for vacuum removal of residue as in claim 13, wherein the single block comprises a plastic block that defines the manifold, the plurality of sample ports, the vacuum port, and the at least one channel.

* * * * *